US012303506B2

(12) United States Patent
Chilakala et al.

(10) Patent No.: US 12,303,506 B2
(45) Date of Patent: May 20, 2025

(54) TRABECTEDIN COMPOSITION

(71) Applicant: EXTROVIS AG, Baar (CH)

(72) Inventors: Krishna Mohan Chilakala, Hyderabad (IN); Nagamalleswara Rao Beeraka, Hyderabad (IN); Ramesh Mantri, Sangareddy (IN); Hanumantha Rao Kamma, Baar (CH); Janos Vaczi, Kuessnacht am Rigi (CH)

(73) Assignee: EXTROVIS AG, Baar (CH)

( * ) Notice: Subject to any disclaimer, the term of this patent is extended or adjusted under 35 U.S.C. 154(b) by 158 days.

(21) Appl. No.: 17/931,831

(22) Filed: Sep. 13, 2022

(65) Prior Publication Data

US 2023/0226051 A1 Jul. 20, 2023

(30) Foreign Application Priority Data

Jan. 20, 2022 (IN) .............................. 202221003332

(51) Int. Cl.
*A61K 31/4995* (2006.01)
*A61K 9/00* (2006.01)
*A61K 9/08* (2006.01)
*A61K 47/10* (2017.01)
*A61K 47/12* (2006.01)
*A61K 47/18* (2017.01)

(52) U.S. Cl.
CPC ........ *A61K 31/4995* (2013.01); *A61K 9/0019* (2013.01); *A61K 9/08* (2013.01); *A61K 47/10* (2013.01); *A61K 47/12* (2013.01); *A61K 47/183* (2013.01)

(58) Field of Classification Search
CPC .... A61K 31/4995; A61K 9/0019; A61K 9/08; A61K 47/10; A61K 47/12; A61K 47/183; A61P 35/00
See application file for complete search history.

(56) References Cited

U.S. PATENT DOCUMENTS

| | | | |
|---|---|---|---|
| 5,256,663 A | 10/1993 | Rinehart et al. | |
| 5,721,362 A | 2/1998 | Corey et al. | |
| 8,119,638 B2 | 2/2012 | Cvitkovich et al. | |
| 8,895,557 B2 | 11/2014 | Beijnen et al. | |
| 9,931,458 B1 | 4/2018 | Di Naro | |
| 10,322,183 B2 | 6/2019 | Beijnen et al. | |
| 10,610,529 B2 * | 4/2020 | Wang | A61K 47/02 |
| 2021/0169873 A1 * | 6/2021 | Kovi | A61K 31/4748 |
| 2021/0361644 A1 | 11/2021 | Kovi et al. | |

FOREIGN PATENT DOCUMENTS

| | | | |
|---|---|---|---|
| IN | 201741041173 A | 12/2019 | |
| WO | 2000069441 A1 | 11/2000 | |
| WO | 2020261301 A1 | 12/2020 | |
| WO | WO-2021209545 A1 * | 10/2021 | ......... A61K 31/4995 |

OTHER PUBLICATIONS

Liang et al., Insight into pyrolysis mechanism of 1,2-propylene glycol: Based on density functional theory and wavefunction analysis, J. Mol. Graph. & Model., 116, paper 108277, pp. 1-10 (Year: 2022).*
2015 Yondelis (trabectedin) drug label, obtained from the url dailymed.nlm.nih.gov/dailymed/drugInfo.cfm?setid=472bd78e-be17-4b9d-90f4-9482c3aec9ff (Year: 2015).*
Janssen Pharmaceutical Companies "Label: Yondelis (trabectedin) for injection, for intravenous use," U.S. Food and Drug Administration, Jun. 3, 2020, Labeling-Package Insert <https://www.accessdata.fda.gov/drugsatfda_docs/label/2020/207953s006lbl.pdf>.

* cited by examiner

*Primary Examiner* — Jeffrey S Lundgren
*Assistant Examiner* — Alexander K. Showalter
(74) *Attorney, Agent, or Firm* — MEDLER FERRO WOODHOUSE & MILLS PLLC

(57) ABSTRACT

The present disclosure provides a stable, ready-to-dilute injectable pharmaceutical composition comprising trabectedin and at least one pharmaceutically acceptable excipient, wherein the composition is free of ethanol.

10 Claims, No Drawings

TRABECTEDIN COMPOSITION

The present disclosure provides a stable, ready-to-dilute injectable pharmaceutical composition comprising trabectedin and at least one pharmaceutically acceptable excipient, wherein the composition is free of ethanol.

BACKGROUND

Trabectedin (Ecteinascidin-743, ET-743) is a tetrahydroisoquinoline alkaloid initially isolated from a marine organism *Ecteinascidia turbinata*, that is now mainly prepared by chemical synthesis. It is an alkylating drug with the chemical name (1'R,6R,6aR,7R,13S,14S,16R)-5(acetyloxy)-3',4',6,6a,7,13,14,16-octahydro-6',8,14-trihydroxy-7',9-dimethoxy-4,10,23 trimethylspiro[6,16-(epithiopropanoxymethano)-7,13-imino-12H-1,3dioxolo[7,8]isoquino[3,2b][3]benzazocine-20,1'(2'H)-isoquinolin]-19-one. Trabectedin has the following chemical structure—

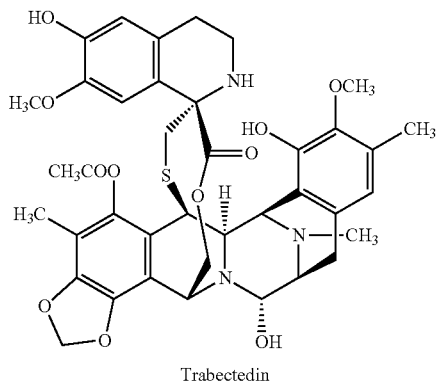

Trabectedin

Trabectedin is an anticancer medicine that interferes with the growth and spread of cancer cells in the body. Trabectedin has been approved as YONDELIS© for use in the treatment of liposarcoma, a rare type of cancer that grows in fatty tissues of the body. The USFDA approved prescribing information for trabectedin states that the product is approved for the treatment of patients with unresectable or metastatic liposarcoma or leiomyosarcoma who received a prior anthracycline-containing regimen. The recommended dose is 1.5 mg/m$^2$ administered as an intravenous infusion over 24 hours through a central venous line every 21 days (3 weeks), until disease progression or unacceptable toxicity.

A synthetic process for producing ecteinascidin compounds is described in U.S. Pat. No. 5,721,362. The claimed method involves many steps, there being multiple examples, each describing one or more steps in the synthetic sequence to arrive at ecteinascidin 743. Further, U.S. Pat. No. 5,256,663 discloses a pharmaceutical composition comprising ET-743 in combination with a pharmaceutically acceptable carrier, diluent or excipient.

Trabectedin has limited aqueous solubility. The instability of trabectedin in aqueous solution has necessitated lyophilization of bulk solutions, in order to increase the storage stability of the pharmaceutical product. The trabectedin preparations required for parenteral administration are currently available only in the form of a lyophilizate (marketed as YONDELIS©), which must be reconstituted before administration to the patient.

PCT publication No. WO 200069441 discloses a sterile lyophilised product of ET-743 with mannitol and a phosphate buffer. This formulation is unstable at refrigerated conditions, as well as at room temperature, and should therefore be stored between −15 and −25° C., protected from light.

In order to overcome certain disadvantages associated with the mannitol containing formulations, U.S. Pat. No. 8,895,557 discloses preparation of a lyophilized composition that comprises an ecteinascidin and a disaccharide. The disaccharide containing formulation was found to provide long term storage of the trabectedin lyophilised formulation over a wide temperature range.

Further, PCT publication No. WO 2021209545 discloses lyophilized formulations comprising trabectedin and an amino acid.

However, the use of such freeze-dried or lyophilized preparations has considerable disadvantages. First of all, the process of preparing these lyophilizates is complicated and are cost intensive over the entire lifecycle of the product. Secondly, reconstitution requires sterile diluent and results in additional requirement for handling by the healthcare personnel administering the drug. Trabectedin being a cytotoxic drug, requires special handling and disposal procedures. Thus, the step of reconstitution requires dedicated space for conducting the operation under sterile and laminar conditions, and it increases the risk of the personnel coming in contact with the cytotoxic drug. Furthermore, other errors in the handling of these lyophilizates can lead to serious problems, such as deviation in the concentration of the active substance leading to dosing errors, or microbial contamination of the solution during the reconstitution step. It is also important to note that provision of a lyophilized product means increased oncologic waste to be handled, which increases the burden on the facility handling the drug administration.

U.S. Patent Publication Nos. 20210169873 and 20210361644 provide ready-to-use liquid parenteral formulations of trabectedin containing ethanol as a solvent. The formulations were reported to be stable at a pH of about 6.5 to about 7.3. Ethanol, which is essential to the solubility and stability of the compositions of the present disclosure, is a central nervous system (CNS) depressant. Symptoms of mild to moderate ethanol intoxication in adults can include euphoria, ataxia, sedation, aggressive behaviour, nausea and vomiting. At high doses it can also cause respiratory depression or failure, and cardiovascular toxicities. Moreover, ethanol use in adult medicines is discouraged for a number of other reasons including interactions with other medicines, diseases, effect on driving performances, issues with addiction, pregnancy and breast feeding etc. Thus, it would be advisable to provide compositions that do not contain ethanol. Unfortunately, the disclosed compositions of these publications also fail to provide trabectedin liquid formulations with long term stability. Para 0051 of US 20210169873 states that the storage-stable ready-to-use Trabectedin formulations for injection may retain at least 90% of the potency of Trabectedin after storage for 12 months at 5° C.±3° C. Further, the working examples provide limited stability data of the injection compositions—all of which contain ethanol—at 14 days and 1 month storage at 25° C./60% relative humidity. There is nothing in these publications that provide long term stability data, nor accelerated stability data reflecting on the shelf life and impurity profile of these trabectedin compositions. There is also nothing in these specifications that can provide a skilled person with any teaching, motivation or reasonable expectation of success in obtaining a stable trabectedin liquid composition without ethanol.

In view of the potential of trabectedin formulations as antitumoral agents, there is a need to provide a composition that can solve problems that conventional compositions and manufacturing methodologies do not possess, or do not completely solve. Thus, there is a need for a stable, ready-to-dilute liquid parenteral composition of trabectedin that is free of solvents like ethanol, and which avoids reconstitution of the product by healthcare professionals.

SUMMARY OF THE INVENTION

The present disclosure provides a stable ready-to-dilute injectable composition comprising trabectedin and a pharmaceutically acceptable excipient.

The present disclosure further provides a stable injectable composition comprising trabectedin, at least one pharmaceutically acceptable solvent, at least one pharmaceutically acceptable co-solvent, and optionally at least one pharmaceutically acceptable stabilizing agent, wherein the composition is ready-to-dilute and is free of ethanol.

The present disclosure also provides a stable ready-to-dilute injectable pharmaceutical composition comprising trabectedin, at least one pharmaceutically acceptable solvent and at least one pharmaceutically acceptable co-solvent, wherein the composition is free of ethanol.

In a preferred embodiment, the ready-to-dilute composition of the present disclosure containing trabectedin comprises a solvent selected from the group consisting of propylene glycol, polyethylene glycol, propanol, butanol, dimethyl formamide, dimethyl acetamide, and dimethyl sulfoxide.

In another preferred embodiment, the ready-to-dilute composition of the present disclosure containing trabectedin contains one or more pharmaceutically acceptable stabilizing agents.

In another preferred embodiment, the ready-to-dilute composition of the present disclosure containing trabectedin comprises a co-solvent. The co-solvent may also function as a solubilizing agent and/or a pH adjusting agent. The co-solvent is selected from the group consisting of acetic acid, glacial acetic acid, tartaric acid, succinic acid, lactic acid, benzene sulfonic acid, citric acid, maleic acid, monobasic sodium phosphate, dibasic sodium phosphate, and sulfuric acid.

In another preferred embodiment, the ready-to-dilute composition of the present disclosure containing trabectedin has a pH of about 2.5 to about 5.0.

In a preferred embodiment, the ready-to-dilute composition of the present disclosure containing trabectedin is stable over a period of 24 months upon storage at about 2° C. to about 8° C.

DETAILED DESCRIPTION

Ecteinascidins, including ET-743, are complex chemical entities whose behaviour in formulations is not predictable in terms of the interaction with other chemical substances. Such behaviour is even more difficult to predict when at least one ecteinascidin is to be included as the active substance to prepare a stable composition.

The present disclosure provides a stable, ethanol free, ready-to-dilute, liquid parenteral composition of trabectedin that is stable and has total impurities controlled within acceptable limits.

The United States Pharmacopoeia (USP) defines stability as "the ability of a product to retain its characteristics that it possessed during its manufacturing (physical, chemical, microbiological, therapeutic properties) within specified limits throughout its period of storage and use". According to the ICH guidelines, pharmaceutical stability testing is defined as "systematic experiments conducted on pharmaceutical products to understand and provide evidence how the quality of a drug product varies under the influence of variety of environmental factors such as temperature, humidity and light, and to set re-test period for the drug, or a shelf life for the drug product and recommend good storage conditions". In view of these, degradation products in a drug product are required to be evaluated and reported to the regulatory agencies. Further, USFDA requires parenteral formulations to be stable for a minimum period of 12 months (i.e. 48 weeks) at recommended storage condition, for approving the same for commercial use. For products to be commercially marketed in the US, there is an expectation that the products will comply to the standard throughout the shelf life.

Therefore, in a first aspect of the present disclosure, ready-to-dilute trabectedin compositions with excellent storage stability are described. The compositions of the present disclosure are stable when stored at 2-8° C. over its shelf life. The term "shelf life", as used herein, refers to the amount of time the pharmaceutical composition may be stored without loss of potency and/or performance profile, i.e. compositions that stay within the specification defined herein, upon storage at about 2° C. to about 8° C. for 3 months, and/or at about 25° C. for 3 months. The stable compositions provided herein are designed to have shelf life of at least 12 months, 24 months or 36 months. Preferred embodiments of the present disclosure have a shelf life of at least about 24 months.

The ready-to-dilute trabectedin compositions of the present disclosure contain less than about 3% of total impurities, preferably less than about 2% of total impurities, preferably less than about 1.8% of total impurities, preferably less than about 1.7% of total impurities, preferably less than about 1.6% of total impurities, more preferably less than about 1.5% of total impurities. The main identified impurities of trabectedin are dehydroxy trabectedin and desacetyl trabectedin. Dehydroxy Trabectedin has the IUPAC name Spiro(6,16-(epithiopropanoxymethano)-7,13-imino-12H-1,3-dioxolo[7,8]isoquino[3,2-b][3]benzazocine-20,1'(2'H)-isoquinolin]-19-one,5-(acetyloxy)-3',4',6,6a7,13,14,16,-octahydro-6',8-dihydroxy-7',9-dimethoxy-4,10,23-trimethyl-,(1'R,6R,6aR,7R,13S,16R) and has the following structure:

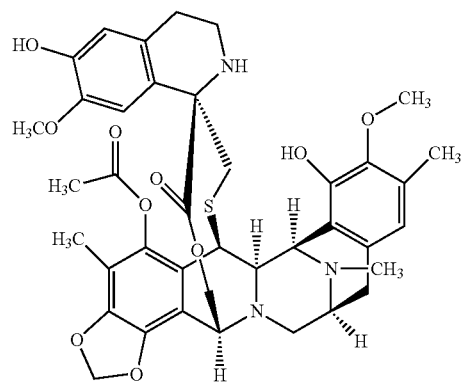

Dehydroxy Trabectedin

Desacetyl trabectedin is chemically known as Spiro[6,16-(epithiopropanoxymethano)-7,13-imino-12H-1,3-dioxolo[7,8]isoquino[3,2-b[3]benzazocine-20,1'(2'H)-isoquinolin]19-one, 3',4',6,6a,7,13,14,16-octahydro-5,6',8,14-tetrahydroxy-7',9-dimethoxy-4,10,23-trimethyl-(1'R,6R,6aR,7R,13S,14S,16R), and has the following chemical structure:

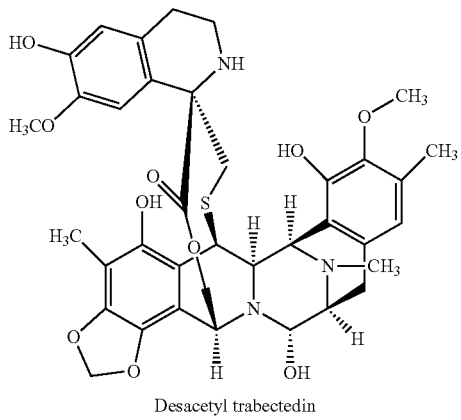 [SMILES: COc1cc2c(cc1O)CCN[C@]21CS[C@@H]2c3c(O)c(C)c4c(c3[C@H](COC1=O)N1[C@@H]2[C@H]2c3c(cc(C)c(OC)c3O)C[C@@H]([C@@H]1O)N2C)OCO4]

Desacetyl trabectedin

In one embodiment, at least about 90% purity of the trabectedin is retained after storage at 2-8° C. at the end of 24 months. More preferably, at least about 92% purity of the trabectedin is retained after storage at 2-8° C. at the end of 24 months. More preferably, at least about 94% purity of the trabectedin is retained after storage at 2-8° C. at the end of 24 months. Still more preferably, at least about 96% purity of the trabectedin is retained after storage at 2-8° C. at the end of 24 months. Most preferably, at least about 98% purity of the trabectedin is retained after storage at 2-8° C. at the end of 24 months.

Preferred stable ready-to-dilute compositions of trabectedin of the present disclosure are stable such that upon storage at 2-8° C. and/or at 25° C. for 3 months, the total impurities are not more than 3% by weight of the composition, the desacetyl impurity is not more than 0.5% by weight of the composition, and the dehydroxy impurity is not more than 0.5% by weight of the composition.

In another aspect of the present disclosure, the ready-to-dilute compositions of trabectedin comprise at least one pharmaceutically acceptable solvent, at least one pharmaceutically acceptable pH adjusting agent and optionally at least one pharmaceutically acceptable stabilizing agent, wherein the composition is free of ethanol.

In yet another aspect of the present disclosure, the ready-to-dilute compositions of trabectedin comprise at least one pharmaceutically acceptable solvent and at least one pharmaceutically acceptable pH adjusting agent, wherein the composition is free of ethanol and free of stabilizing agent.

In preferred embodiments the composition has a concentration of trabectedin of about 0.05 mg/ml.

The solvent used in the compositions of the present disclosure may be selected from, but is not limited to, the group comprising propylene glycol, polyethylene glycol, propanol, butanol, t-butanol, dimethyl acetamide, solketal, glycerol formal, acetone, glycerol, glycofurol, diethylene glycol monoethyl ether, dimethyl sulfoxide, N-methyl-2-pyrrolidone, water for injection, dimethyl formamide, aqueous solutions of disaccharides and mixtures thereof. The solvent used in the composition of the present disclosure is not ethanol, and the compositions of the present disclosure are free of ethanol.

In preferred embodiments, the solvent is propylene glycol. In another embodiment the solvent is dimethylacetamide. In another embodiment the solvent is polyethylene glycol. In yet another embodiment the solvent is propanol. In another embodiment the solvent is butanol. In another embodiment the solvent is dimethyl formamide. In a highly preferred embodiment of the present disclosure, the solvent used is propylene glycol. It helps to dissolve the trabectedin, thereby providing compositions of trabectedin that are physically and chemically stable over its shelf life.

In one embodiment, the composition has an amount of solvent(s) from about 0.001 ml to about 1 ml. More preferably, the composition has an amount of solvent from about 0.01 ml to about 1 ml. More preferably, the composition has an amount of solvent about 0.01 ml, about 0.02 ml, about 0.03 ml, about 0.04 ml, about 0.05 ml, about 0.06 ml, about 0.07 ml, about 0.08 ml, about 0.09 ml, about 0.1 ml, about 0.2 ml, about 0.3 ml, about 0.4 ml, about 0.5 ml, about 0.6 ml, about 0.7 ml, about 0.8 ml, about 0.9 ml or about 1 ml.

The pH is critical to stability of the ready-to-dilute compositions of the present disclosure. In preferred embodiments, the compositions have a pH of about 2.5 to about 5. More preferably, the compositions have a pH ranging from about 2.5 to about 4.5. More preferably, the compositions have a pH of about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9 or about 5. The desired pH is obtained by adding a pH adjusting agent to the compositions of the present disclosure.

The pH adjusting agent may be selected from, but is not limited to, the group consisting of acetic acid, glacial acetic acid, tartaric acid, lactic acid, hydrochloric acid, benzene sulfonic acid, boric acid, citric acid, triethanolamine, ortho-phosphoric acid, succinic acid, fumaric acid, monoethanolamine, sodium carbonate, sodium bicarbonate, diethanolamine, magnesium aluminium silicates, maleic acid, malic acid, sodium hydroxide, magnesium oxide, calcium carbonate, monobasic sodium phosphate, gluconic acid, tartaric acid, dibasic sodium phosphate, magnesium carbonate, sulfuric acid and mixtures thereof.

In one embodiment, the composition uses the pH adjusting agent in an amount ranging from about 0.01 mg to 5 mg. More preferably, the composition contains about 0.01 mg to about 4 mg, about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, or about 5 mg of the pH adjusting agent. The pH-adjusting agent is used in an amount sufficient to provide the desired pH of about 2.5 to about 5.0. In preferred embodiments the pH adjusting agent is lactic acid, which also acts as a solubilizing agent.

In another embodiment, the ready-to-dilute composition contains one or more stabilizing agents. The stabilizing agent is typically an amino acid selected from, but not limited to, the group consisting of glycine, L-arginine, phenylalanine, histidine, acetylcysteine, citrulline, lysine, isoleucine, methionine, cysteine and their pharmaceutically acceptable salts, and combinations thereof.

In one embodiment, the stabilizing agent is L-arginine. In another embodiment, the stabilizing agent is glycine. In yet another embodiment, the stabilizing agent is phenylalanine. In still another embodiment, the stabilizing agent used is histidine.

In preferred embodiments, the amount of stabilizing agent in the composition is about 0.05 mg to 10 mg. More preferably the composition contains about 0.06 mg, preferably about 0.07 mg, preferably about 0.08 mg, preferably about 0.09 mg, preferably about 0.1 mg, preferably about 0.2 mg, preferably about 0.3 mg, preferably about 0.4 mg, preferably about 0.5 mg, preferably about 0.6 mg, preferably about 0.7 mg, preferably about 0.8 mg, preferably about 0.9 mg, preferably about 1 mg, preferably about 1.5 mg, preferably about 2 mg, preferably about 2.5 mg, preferably about 3 mg, preferably about 3.5 mg, preferably about 4 mg, preferably about 4.5 mg, preferably about 5 mg, preferably about 6 mg, preferably about 7 mg, preferably about 8 mg, preferably about 9 mg or preferably about 10 mg of the stabilizing agent.

In some embodiments, the ready-to-dilute compositions of the present disclosure include an antioxidant selected from the group consisting of salts of sulfur oxide including bisulfite, metabisulfite and sulfite, BHA, BHT and mixtures thereof.

According to the present disclosure, the ready-to-dilute composition typically comprises 0.05 mg/ml of trabectedin. The composition of the present disclosure may be provided in a vial or a similar container. Any suitable sterile vial or container that is compatible with sterile storage of trabectedin for extended periods of times may be used. Suitable containers are those that are typically used for packaging of sterile pharmaceutical compositions, such as those made from type I colorless glass vials, polyvinylchloride (PVC) and polyethylene (PE) bags, PE and polypropylene (PP) mixture bags, and the like.

The ready-to-dilute compositions of the present disclosure may also be packaged in prefilled syringes (PFS) or in cartridges for autoinjectors. The material of construction of the prefilled syringes and cartridges is such that stability of the trabectedin composition of the present disclosure is not compromised over its shelf-life. It may be made up of a material selected from glass, plastic or a polymeric material. In preferred embodiments, the material of construction is glass, such as USP Type I clear glass or non-pyogenic glass. In other embodiments, the material of construction is non-glass plastic or polymeric material selected from cycloolefin polymer, cycloolefin copolymer, polypropylene, polyolefins, styrene-polyolefin based polymers and block co-polymers, polycarbonates and the like.

In one embodiment of the present disclosure, the stable ready-to-dilute pharmaceutical composition comprises about 0.05 mg/ml of trabectedin, about 0.05 ml/ml to about 0.1 ml/ml of propylene glycol and sterile water for injection, wherein the composition has a pH of about 2 to about 5.

In another embodiment of the disclosure, the stable ready-to-dilute pharmaceutical composition comprises about 0.05 mg/ml of trabectedin, about 0.05 ml/ml to about 0.1 ml/ml propylene glycol, about 0.5 mg to 3.5 mg of glycine and sterile water for injection, wherein the composition has a pH of about 2 to about 5.

In yet another embodiment of the present disclosure, the stable ready-to-dilute pharmaceutical composition comprises about 0.05 mg/ml of trabectedin, about 0.05 ml/ml to about 0.1 ml/ml propylene glycol, about 0.5 mg to 3.5 mg of L-arginine and sterile water for injection, wherein the composition has a pH of about 2.5 to about 5.

In another embodiment of the present disclosure, the stable ready-to-dilute pharmaceutical composition comprises about 0.05 mg/ml of trabectedin, about 0.05 ml/ml to about 0.1 ml/ml propylene glycol, about 0.5 mg to 3.5 mg of lactic acid and sterile water for injection, wherein the composition has a pH of about 2.5 to about 5.

It must be noted that the ready-to-dilute compositions of the present disclosure are prepared for administration to a patient by diluting the required dose of trabectedin with 500 ml of 0.9% Sodium Chloride, USP, or 5% Dextrose injection, USP. The diluted solution may be administered over 24 hours through a central venous line using an infusion set with a 0.2 micron polyethersulfone (PES) in-line filter to reduce the risk of exposure to adventitious pathogens that may be introduced during the dilution process.

Definitions

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the invention.

Unless the context indicates otherwise, it is specifically intended that the various features of the disclosure described herein can be used in any combination.

Moreover, the present disclosure also contemplates that in some embodiments of the disclosure, any feature or combination of features set forth herein can be excluded or omitted.

All publications, patent applications, patents, and other references mentioned herein are incorporated by reference herein in their entirety for all purposes.

As used herein, "a," "an," or "the" can mean one or more than one.

Also as used herein, "and/or" refers to and encompasses any and all possible combinations of one or more of the associated listed items, as well as the lack of combinations when interpreted in the alternative ("or").

As used herein, the term "excipient" refers to substantially inert materials that are nontoxic and do not interact with other components of a composition in a deleterious manner and which are approved by regulatory authorities or are generally regarded as safe for human or animal use.

Furthermore, the term "about", as used herein, when referring to a measurable value such as an amount of a compound or agent of this disclosure, dose, time, temperature, and the like, is meant to encompass variations of ±10% of the specified amount.

The term "ready-to-dilute" when used in connection with a trabectedin composition refers to a composition that includes trabectedin in dissolved or solubilized form, and may be used as such, or upon further dilution with intravenous diluents.

As used herein, and unless otherwise specified, the term "stable" refers to physical and chemical stability of the composition over the shelf-life of the composition.

The term "acceptable level of impurity" refers to the impurities in drug products not exceeding the permitted daily exposure (PDE), and/or impurities within limits defined by ICH for pharmaceutical products.

The present disclosure is further illustrated by reference to the following examples which is for illustrative purposes only, and does not limit the scope of the disclosure in any manner.

Example 1

| Ingredient | F-1 | F-2 | F-3 |
|---|---|---|---|
| | Quantity/ml | | |
| Trabectedin | 0.05 mg | 0.05 mg | 0.05 mg |
| Propylene glycol | 0.1 mL | 0.05 mL | 0.05 mL |
| Lactic acid | 2 mg | 2 mg | 0.5 mg |
| Glycine | 2.5 mg | 2.5 mg | 2.5 mg |
| Water for Injection | Q.S. to 1 mL | Q.S. to 1 mL | Q.S. to 1 mL |

Propylene glycol was dispensed in a compounding vessel and trabectedin was added under stirring. The stirring was continued until a clear solution was obtained. About 80% of the total required water was then added and stirring was continued. This was followed by addition of the required quantity of lactic acid to the solution under stirring. Glycine was then added to the solution thus obtained, and stirring was continued. The volume was made up to the required batch quantity by adding remaining water for injection, and stirred to get a uniform clear solution. The pH of the solution was measured and was found to be in the range of 3-3.5. The final solution was then filtered using a 0.22p PES membrane filter. The filtered solution was filled into type-1 clear glass vials (Fill Vol: 2 mL) and stoppered with 13 mm premium coat bromobutyl stoppers and flip off aluminium seals. The entire process was carried out under aseptic manufacturing conditions. The vials were then subjected to stability testing. The stability data is provided in Tables 1 to 3 below for all the three compositions of Example 1.

TABLE 1

Stability data of Composition F-1

| | | Batch No Composition F-1 Condition | | | | | | |
|---|---|---|---|---|---|---|---|---|
| | | 40° C. | 2-8° C. | | | 25 ± 2° C./60 ± 5% RH | | |
| Parameter | Initial | 2 Weeks | 2 Weeks | 1 Month | 3 Months | 2 Weeks | 1 Month | 3 Months |
| Description | CCS | CCS | CCS | CCS | CCS | CCS | CCS | CCS |
| pH | 3.24 | 3.44 | 3.21 | 3.05 | 3.20 | 3.22 | 3.22 | 3.21 |
| Assay | Not analysed | 85.7 | 93.0 | 94.0 | 93.9 | 92.1 | 91.2 | 90.5 |
| UK Impurity @ 0.15 | ND | 0.26 | ND | ND | ND | BDL | BDL | 0.43 |
| Trabectedin desacetyl impurity @ RRT~0.75 | 0.14 | 0.06 | 0.15 | 0.23 | 0.31 | 0.23 | 0.32 | 0.31 |
| Trabectedin dehydroxy impurity @ RRT~1.10 | BDL | BDL | BDL | BDL | BDL | BDL | BDL | BDL |
| Max UK Imp | BDL | 0.21 | 0.07 | 0.13 | BDL | BDL | 0.12 | 0.07 |
| Total Impurities | 0.20 | 1.25 | 0.38 | 0.77 | 0.44 | 0.31 | 1.16 | 1.01 |

ND: Not Detected; CCS: Clear Colorless Solution; BDL: Below Detection Limit; RH: Relative humidity; UK: Unknown

TABLE 2

Stability data of Composition F-2

| | | Batch No Composition F-2 Condition | | | | | |
|---|---|---|---|---|---|---|---|
| | | 40° C. | 2-8° C. | | 25 ± 2° C./60 ± 5% RH | | |
| Parameter | Initial | 2 Weeks | 2 Weeks | 1 Month | 2 Weeks | 1 Month | |
| Description | CCS | CCS | CCS | CCS | CCS | CCS | |
| pH | 3.22 | 3.32 | 3.21 | 3.00 | 3.23 | 3.02 | |
| Assay | 96.8 | 94.4 | 97.5 | 96.6 | 96.0 | 95.3 | |
| UK Impurity @ 0.15 | ND | 0.39 | ND | ND | 0.06 | 0.11 | |
| Trabectedin desacetyl impurity @ RRT~0.75 | 0.07 | 0.35 | 0.11 | 0.25 | 0.28 | 0.46 | |
| Trabectedin dehydroxy impurity @ RRT~1.10 | BDL | BDL | BDL | BDL | BDL | BDL | |

TABLE 2-continued

Stability data of Composition F-2

| | Batch No Composition F-2 Condition | | | | | |
|---|---|---|---|---|---|---|
| | 40° C. | | 2-8° C. | | 25 ± 2° C./60 ± 5% RH | |
| Parameter | Initial | 2 Weeks | 2 Weeks | 1 Month | 2 Weeks | 1 Month |
| Max UK Imp | BDL | BDL | BDL | BDL | BDL | 0.10 |
| Total Impurities | 0.20 | 1.07 | 0.22 | 0.37 | 0.45 | 0.83 |

ND: Not Detected; CCS: Clear Colorless Solution; BDL: Below Detection Limit; RH: Relative humidity; UK: Unknown

TABLE 3

Stability data of Composition F-3

| | Batch No Composition F-3 Condition | | | | | |
|---|---|---|---|---|---|---|
| | 2-8° C. | 40° C. | 2-8° C. | | 25 ± 2° C./60 ± 5% RH | |
| Parameter | Initial | 2 Weeks | 2 Weeks | 1 Month | 2 Weeks | 1 Month |
| Description | CCS | CCS | CCS | CCS | CCS | CCS |
| pH | 3.45 | 3.60 | 3.50 | 3.56 | 3.56 | 3.69 |
| Assay | 98.7 | 92.8 | 98.4 | 98.6 | 97.6 | 96.2 |
| UK Impurity @ 0.15 | ND | 0.67 | BDL | BDL | 0.12 | 0.19 |
| Trabectedin desacetyl impurity @ RRT~0.75 | 0.11 | 0.28 | 0.26 | 0.21 | 0.31 | 0.38 |
| Trabectedin dehydroxy impurity @ RRT~1.10 | BDL | 0.14 | BDL | BDL | BDL | BDL |
| Max UK Imp | BDL | 0.22 | BDL | BDL | 0.12 | 0.11 |
| Total Impurities | 0.26 | 1.52 | 0.39 | 0.36 | 0.69 | 0.77 |

ND: Not Detected; CCS: Clear Colorless Solution; BDL: Below Detection Limit; RH: Relative humidity; UK: Unknown Example 2

| Ingredient | Quantity/mL F-4 |
|---|---|
| Trabectedin | 0.05 mg |
| Propylene glycol | 0.05 mL |
| Lactic acid | 0.5 mg |
| L-Arginine | 0.5 mg |
| Water for Injection | Q.S. to 1 mL |

The composition F-4 was obtained by a process similar to that described above in Example 1. The vials were loaded into stability chambers as per the stability protocol. The stability data is provided in Table 4 below for the composition of Example 2.

TABLE 4

Stability data of Composition F-4

| | Batch No Composition F-4 Condition | | | | | |
|---|---|---|---|---|---|---|
| | 2-8° C. | 40° C. | 2-8° C. | | 25 ± 2° C./60 ± 5% RH | |
| Parameter | Initial | 2 Weeks | 2 Weeks | 1 Month | 2 Weeks | 2 Weeks |
| Description | CCS | CCS | CCS | CCS | CCS | CCS |
| pH | 4.08 | 4.24 | 4.57 | 4.30 | 4.13 | 4.23 |

TABLE 4-continued

Stability data of Composition F-4

| | Batch No Composition F-4 Condition | | | | | |
|---|---|---|---|---|---|---|
| | 2-8° C. | 40° C. | 2-8° C. | | 25 ± 2° C./60 ± 5% RH | |
| Parameter | Initial | 2 Weeks | 2 Weeks | 1 Month | 2 Weeks | 2 Weeks |
| Assay | 92.4 | 86.6 | 91.7 | 92.6 | 90.9 | 90.1 |
| UK Impurity @ 0.15 | ND | 1.81 | 0.12 | BDL | 0.36 | 0.55 |
| Trabectedin desacetyl impurity @ RRT~0.75 | 0.12 | 0.20 | 0.16 | 0.16 | 0.18 | 0.16 |
| Trabectedin dehydroxy impurity @ RRT~1.10 | 0.05 | 0.09 | BDL | BDL | BDL | BDL |
| Max UK Imp | 0.05 | 0.26 | BDL | BDL | 0.05 | 0.08 |
| Total Impurities | 0.31 | 2.53 | 0.50 | 0.34 | 0.63 | 0.85 |

ND: Not Detected; CCS: Clear Colorless Solution; BDL: Below Detection Limit; RH: Relative humidity; UK: Unknown Example 3

| Ingredient | Quantity/mL F-5 |
|---|---|
| Trabectedin | 0.05 mg |
| Propylene glycol | 0.1 mL |
| Lactic acid | 1 mg |
| Water for Injection | Q.S. to 1 mL |

Propylene glycol was dispensed into a compounding vessel, and to it was added trabectedin with stirring. The stirring was continued until a clear solution was obtained. To this was added about 80% of the required water for injection under stirring, and stirring was continued to get a clear solution. The required quantity of lactic acid was then added to this solution under stirring. The volume was made up by then adding the remaining quantity of water for injection, and the mixture was stirred until a clear solution was obtained. The pH of the solution was measured at this stage and was found to be in the range of 2.7-3.0. The bulk solution was then filtered using a 0.22p PES membrane filter. The filtered solution was filled into type-1 clear glass vials (Fill Vol: 2 mL) and stoppered with 13 mm premium coat bromobutyl stoppers and flip off aluminium seals. The entire process was carried out under aseptic manufacturing conditions.

The vials were then subjected to stability testing. The stability data is provided in Table 5 below for all the composition F-5.

TABLE 5

Stability data of composition F-5

| | Batch No. Composition F-5 Condition | | | | | |
|---|---|---|---|---|---|---|
| | 40° C. | 2-8° C. | | 25 ± 2° C./60 ± 5% RH | | |
| Parameter | Initial | 2 Weeks | 2 Weeks | 1 Month | 2 Weeks | 1 Month |
| Description | CCS | CCS | CCS | CCS | CCS | CCS |
| pH | 2.90 | 2.92 | 3.04 | 2.75 | 2.92 | 2.79 |
| Assay | 101.1 | 99.5 | 100.7 | 100.5 | 99.5 | 100.9 |
| UK Impurity @ 0.15 | ND | 0.19 | ND | ND | BDL | 0.06 |
| Trabectedin desacetyl impurity @ RRT~0.75 | 0.04 | 0.38 | 0.09 | 0.23 | 0.31 | 0.54 |
| Trabectedin dehydroxy impurity @ RRT~1.10 | BDL | BDL | BDL | BDL | BDL | BDL |
| Max UK Imp | BDL | BDL | BDL | BDL | BDL | BDL |
| Total Impurities | 0.15 | 0.67 | 0.26 | 0.43 | 0.49 | 0.74 |

ND: Not Detected; CCS: Clear Colorless Solution; BDL: Below Detection Limit; RH: Relative humidity; UK: Unknown

Example 4

The composition F3 was subjected to stability testing and samples were analysed by using following method.

Chromatographic condition: A High-Performance Liquid Chromatograph (HPLC) equipped with gradient capacity.

Data handling system: Empower 3 or equivalent chromatographic software

Column: A stainless steel column of length 100 mm, internal diameter 4.6 mm and filled with porous silica particles of 3μ, chemically bonded to octadecyl silane. (Phenomenex Omega polar C18 (100×4.6 mm×3μ))

Preparation of Mobile phase A: 2.70 g of Potassium dihydrogen orthophosphate+3 mL of triethyl amine in 1000 mL of water; pH to 4±0.05 adjusted with diluted Orthophosphoric acid.

Mobile phase B: Filtered and degassed methanol

Preparation of diluent: 1.36 g of Potassium dihydrogen orthophosphate in 1000 mL water, pH to 4±0.05 adjusted with diluted Orthophosphoric acid.

Flow rate: 1.0 ml/min
Detection: UV at 210 nm
Injection volume: 20 μl
Column oven temperature: 40° C.
Auto sampler: 5° C.
Run time: 85 minutes
Rinse solvent: water: ethanol:30:70

A gradient program of Mobile Phase A and Mobile Phase B is run as follows—

| Time | Mobile Phase A | Mobile Phase B |
|---|---|---|
| Initial | 65 | 35 |
| 2.0 | 65 | 35 |
| 25.0 | 50 | 50 |
| 45.0 | 20 | 80 |
| 65.0 | 20 | 80 |
| 66.0 | 65 | 35 |
| 85.0 | 65 | 35 |

The results obtained are summarized in Table 6.

TABLE 6

Stability data of Composition F-3

| Batch No | Composition F-3 | | | | |
|---|---|---|---|---|---|
| Condition Parameter | Initial 2-8° C. | 1M 25° C. | 1M 2-8° C. | 3M 25° C. | 3M 2-8° C. |
| Description | CCS | CCS | CCS | CCS | CCS |
| pH | 3.45 | 3.69 | 3.56 | 3.52 | 3.62 |
| Osmolality (Mosmol/KG) | 158 | NP | NP | NP | NP |
| UK Impurity @ 0.15 | ND | 0.19 | 0.01 | 0.69 | 0.05 |
| Desacetyl impurity @RRT 0.75 | 0.11 | 0.38 | 0.21 | 0.26 | 0.23 |
| Dehydroxy Impurity | 0.02 | 0.04 | 0.03 | 0.03 | 0.09 |
| % Assay | 98.73 | 96.19 | 98.56 | 92.65 | 100.68 |
| Total Impurities | 0.26 | 0.77 | 0.36 | 2.72 | 0.68 |

M = month;
CCS = clear colorless solution;
UK = unknown

The composition F-3 was found to have has not more than 3.0% of total impurities, not more than 0.5% of desacetyl trabectedin impurity and not more than 0.5% of dehydroxy trabectedin impurity, when stored for 3 months at about 2 degrees Celsius to about 8 degrees Celsius, as well as when stored for 3 months at about 25 degrees Celsius. This data, when extrapolated, indicated a shelf life of at least 24 months when stored at about 2 degrees Celsius to about 8 degrees Celsius.

The invention claimed is:

1. A stable ready-to-dilute injectable pharmaceutical composition comprising (i) a therapeutically effective amount of trabectedin of about 0.05 mg/ml and (ii) a pharmaceutically acceptable carrier consisting of one pharmaceutically acceptable solvent, one pharmaceutically acceptable pH-adjusting agent, and one pharmaceutically acceptable stabilizing agent, wherein the composition is free of ethanol, has a pH of about 2.5 to about 5, and wherein when stored for 3 months at about 2 degrees Celsius to about 8 degrees Celsius, or for 3 months at about 25 degrees Celsius, the composition has (a) not more than 3.0% of total impurities, (b) not more than 0.5% of desacetyl trabectedin impurity and (c) not more than 0.5% of dehydroxy trabectedin impurity.

2. The stable ready-to-dilute injectable pharmaceutical composition of claim 1, wherein the solvent is selected from the group consisting of propylene glycol, polyethylene glycol, dimethyl acetamide, solketal, glycerol formal, acetone, glycerol, glycofurol, diethylene glycol monoethyl ether, dimethyl sulfoxide, N-methyl-2-pyrrolidone, water for injection, dimethyl formamide, aqueous solutions of disaccharides and mixtures thereof.

3. The stable ready-to-dilute injectable pharmaceutical composition of claim 2 wherein the solvent is propylene glycol.

4. The stable ready-to-dilute injectable pharmaceutical composition of claim 2, wherein the solvent is present in an amount of about 0.001 ml to about 1 ml per ml of the composition.

5. The stable ready-to-dilute injectable pharmaceutical composition of claim 1, wherein the pH-adjusting agent is selected from the group consisting of acetic acid, glacial acetic acid, tartaric acid, lactic acid, hydrochloric acid, benzene sulfonic acid, boric acid, citric acid, triethanolamine, orthophosphoric acid, succinic acid, fumaric acid, monoethanolamine, sodium carbonate, sodium bicarbonate, diethanolamine, magnesium aluminium silicates, maleic acid, malic acid, sodium hydroxide, magnesium oxide, calcium carbonate, monobasic sodium phosphate, gluconic acid, tartaric acid, dibasic sodium phosphate, magnesium carbonate, sulfuric acid and mixtures thereof.

6. The stable ready-to-dilute injectable pharmaceutical composition of claim 5, wherein the pH-adjusting agent is lactic acid.

7. The stable ready-to-dilute injectable pharmaceutical composition of claim 1, wherein the stabilizing agent is selected from the group consisting of glycine, 1-arginine, phenylalanine, histidine, acetylcysteine, citrulline, lysine, and isoleucine, methionine, cysteine and their pharmaceutically acceptable salts, and mixtures thereof.

8. The stable ready-to-dilute injectable pharmaceutical composition of claim 1 wherein at least about 90% purity of the trabectedin is retained after storage at about 2 degrees Celsius to about 8 degrees Celsius.

9. A stable ready-to-dilute injectable pharmaceutical composition comprising (i) a therapeutically effective amount of trabectedin, (ii) propylene glycol, (iii) lactic acid in an amount sufficient to provide a pH of about 2.5 to 5.0 (iv) glycine and (v) sterile water for injection, and wherein when stored for 3 months at about 2 degrees Celsius to about 8 degrees Celsius, or for 3 months at about 25 degrees Celsius, the composition has (a) not more than 3.0% of total impurities, (b) not more than 0.5% of desacetyl trabectedin impurity and (c) not more than 0.5% of dehydroxy trabectedin impurity.

10. The stable ready-to-dilute injectable pharmaceutical composition of claim 9 wherein at least about 90% purity of the trabectedin is retained after storage at about 2 degrees Celsius to about 8 degrees Celsius.

* * * * *